US 7,803,135 B2

(12) United States Patent
Franer

(10) Patent No.: US 7,803,135 B2
(45) Date of Patent: Sep. 28, 2010

(54) INSERTION DEVICE WITH FLOATING HOUSING AND METHOD OF USE

(75) Inventor: Paul T. Franer, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 192 days.

(21) Appl. No.: 11/771,635

(22) Filed: Jun. 29, 2007

(65) Prior Publication Data

US 2009/0005738 A1  Jan. 1, 2009

(51) Int. Cl.
*A61M 5/178* (2006.01)
(52) U.S. Cl. .................. 604/164.01; 604/264
(58) Field of Classification Search ............ 604/164.01, 604/264
See application file for complete search history.

(56) References Cited

U.S. PATENT DOCUMENTS

| 5,209,737 | A | 5/1993 | Ritchart et al. |
|---|---|---|---|
| 5,308,336 | A | 5/1994 | Hart et al. |
| 5,385,553 | A | 1/1995 | Hart et al. |
| 5,443,452 | A | 8/1995 | Hart et al. |
| 5,476,475 | A | 12/1995 | Gadberry |
| 5,496,280 | A | 3/1996 | Vandenbroek et al. |
| 5,569,205 | A | 10/1996 | Hart et al. |
| 5,584,850 | A | 12/1996 | Hart et al. |
| 5,657,963 | A * | 8/1997 | Hinchliffe et al. ......... 251/149.1 |
| 5,709,664 | A | 1/1998 | Vandenbroek et al. |
| 5,820,600 | A * | 10/1998 | Carlson et al. ......... 604/167.03 |
| 5,989,224 | A * | 11/1999 | Exline et al. ........... 604/167.02 |
| 6,162,196 | A | 12/2000 | Hart et al. |
| 6,217,555 | B1 | 4/2001 | Hart et al. |
| 6,551,282 | B1 * | 4/2003 | Exline et al. ........... 604/167.01 |
| 6,942,671 | B1 * | 9/2005 | Smith .......................... 606/108 |
| 7,083,626 | B2 * | 8/2006 | Hart et al. ................... 606/108 |
| 2003/0139756 | A1 | 7/2003 | Brustad |
| 2004/0068232 | A1 * | 4/2004 | Hart et al. .............. 604/167.06 |

FOREIGN PATENT DOCUMENTS

| WO | WO-9850093 | 11/1998 |
|---|---|---|
| WO | WO-9853865 | 12/1998 |

* cited by examiner

*Primary Examiner*—Nicholas D Lucchesi
*Assistant Examiner*—Gerald Landry, II

(57) ABSTRACT

An insertion device configured for providing access to a treatment site within a body cavity is provided herein. In general, the device includes an elongate cannula configured to receive and allow passage therethrough of a surgical instrument to a treatment site. Additionally, a proximal end of the cannula is movably coupled to a housing thereby facilitating delivery of the instrument therethrough. Additionally, various embodiments of a method for delivering (e.g., laprascopically, endoscopically, etc.) various surgical instruments to various treatment sites via an elongate cannula wherein the cannula includes a proximal end movably coupled to a housing are provided herein.

18 Claims, 5 Drawing Sheets

US 7,803,135 B2

1

INSERTION DEVICE WITH FLOATING HOUSING AND METHOD OF USE

FIELD OF USE

The present invention relates to methods and devices for providing access to a body cavity.

BACKGROUND

Various surgical procedures require accessing a body cavity using a trocar. Typically, a trocar includes an elongate cannula fixedly coupled to a housing that defines a chamber in communication with the inner lumen of the cannula. Once the cannula is positioned within the body cavity, various elongate surgical instruments or tools axially extend into and are withdrawn from the cannula through the proximal end portion of the housing.

In use, it is essential to maintain a substantially closed environment during insertion or withdrawal of the trocar so as to preserve sterility of the treatment site in addition to preventing the escape of liquids and/or insufflation. Typically, a seal element is disposed within the housing in an attempt to provide such an environment. However, the effectiveness of such seals typically diminishes as an instrument is delivered off-axis relative to the cannula because such off-axis delivery results in a disproportionate force being applied to one portion of the seal as opposed to the remainder of the seal. This can result in non-uniform deformation of the seal which can thereby result in contamination of the site and/or escape of liquids and/or insufflation from the cannula.

As such, there remains a need for devices and methods configured to allow for the efficient and reliable off-axis delivery of a surgical instrument to a treatment site.

SUMMARY

Methods and devices are disclosed herein for providing access to a treatment site within a body cavity. In general, the methods and devices include and/or utilize any type of elongate sleeve/cannula (e.g., flexible, non-flexible) configured to allow passage of a surgical device therethrough to a treatment site wherein a proximal end of the cannula is movably coupled to a housing. As such, following positioning of a distal portion of the cannula at the treatment site, the housing can be moved (e.g., angled, tilted, etc) relative to the cannula so as to facilitate insertion and delivery of a surgical instrument to the cannula and ultimately to the treatment site. In those embodiments having a seal(s) fixedly disposed within the housing, the movable coupling can allow for an aperture of the seal to maintain a desired orientation relative to the surgical device so as to maintain an effective seal and therefore a substantially closed embodiment during the surgical procedure.

Various embodiments of the insertion device are provided herein. In one such embodiment, the insertion device includes a cannula having a proximal end, a distal end, and a lumen extending therebetween wherein the lumen is configured to allow for passage of a surgical device to a treatment site. Additionally, the device includes a housing movably coupled to the proximal end of the cannula, and having a lumen therethough in alignment with the lumen in the cannula. In one embodiment, the device further includes at least one seal (e.g., a first seal and a second seal) disposed in the housing and extending across the lumen in the housing wherein the seal(s) can be fixedly disposed within the housing.

2

As will be discussed in detail below, the housing can be movably coupled to the proximal end of the cannula in various manners. In one such embodiment, the housing can be movably coupled to the proximal end of the cannula by a flexible member. The flexible member can include a bellows, a spring, and any other such flexible material.

In another embodiment, a trocar assembly is provided which includes an obturator, and a trocar cannula having a housing and a hollow shaft movably coupled to the housing. Additionally, cannula includes a lumen extending through the housing and the hollow shaft for receiving and guiding the obturator through the trocar cannula.

Similar to above, the housing can be movably coupled to the hollow shaft by a flexible member (e.g., a bellows, a spring, etc.) extending between an open proximal end of the hollow shaft and an opening formed in a distal end of the housing. Additionally, the assembly can include at least one seal (e.g., a first and second seal) disposed in the housing and extending across the lumen in the housing wherein the seal can be fixedly disposed within the housing.

In yet another embodiment, a method for delivering a surgical instrument to a treatment site is provided/For example, the method can include inserting a cannula through tissue such that the cannula provides a working channel extending to a treatment site. Next, the method can include inserting an instrument through the cannula, and further positioning the instrument offset from an axis of the cannula such that a housing movably coupled to the cannula pivots relative to the cannula so as to move with the instrument. Optionally, the cannula can include an obturator disposed therein such that inserting the cannula includes penetrating the obturator with the cannula disposed therearound through tissue. In one embodiment, the housing can include a seal, and the seal can maintain a sealed relationship with the instrument as the housing pivots relative to the cannula.

In other embodiments, the method can provide various sterilization and/or processing procedures. For example, the method can include sterilizing the insertion device after at least one use. In another embodiment, the method can include obtaining an embodiment of the device and/or assembly, sterilizing the assembly, and/or storing the assembly in a sterile container.

BRIEF DESCRIPTION OF THE DRAWINGS

Exemplary embodiments of the invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, the devices provided herein include any type of elongate sleeve/cannula (e.g., flexible, non-flexible) configured to allow passage of a surgical device therethrough to a treatment site wherein a proximal end of the cannula is movably coupled to a housing. As such, following positioning of a distal portion of the cannula at the treatment site, the housing can be moved (e.g., angled, tilted, pivoted, etc.) relative to the cannula so as to facilitate insertion and delivery of a surgical instrument to the cannula and ultimately to the treatment site. The movable coupling can allow the housing and any seal(s) disposed therein to move with the surgical instrument thereby maintaining an effective seal (and therefore a substantially closed environment) during a desired procedure. The device therefore facilitates off-axis delivery of a surgical device to a treatment site while also allowing for a proper seal to be formed and maintained between various seal elements disposed within the housing and the surgical instrument passing therethrough.

Figure 1A:
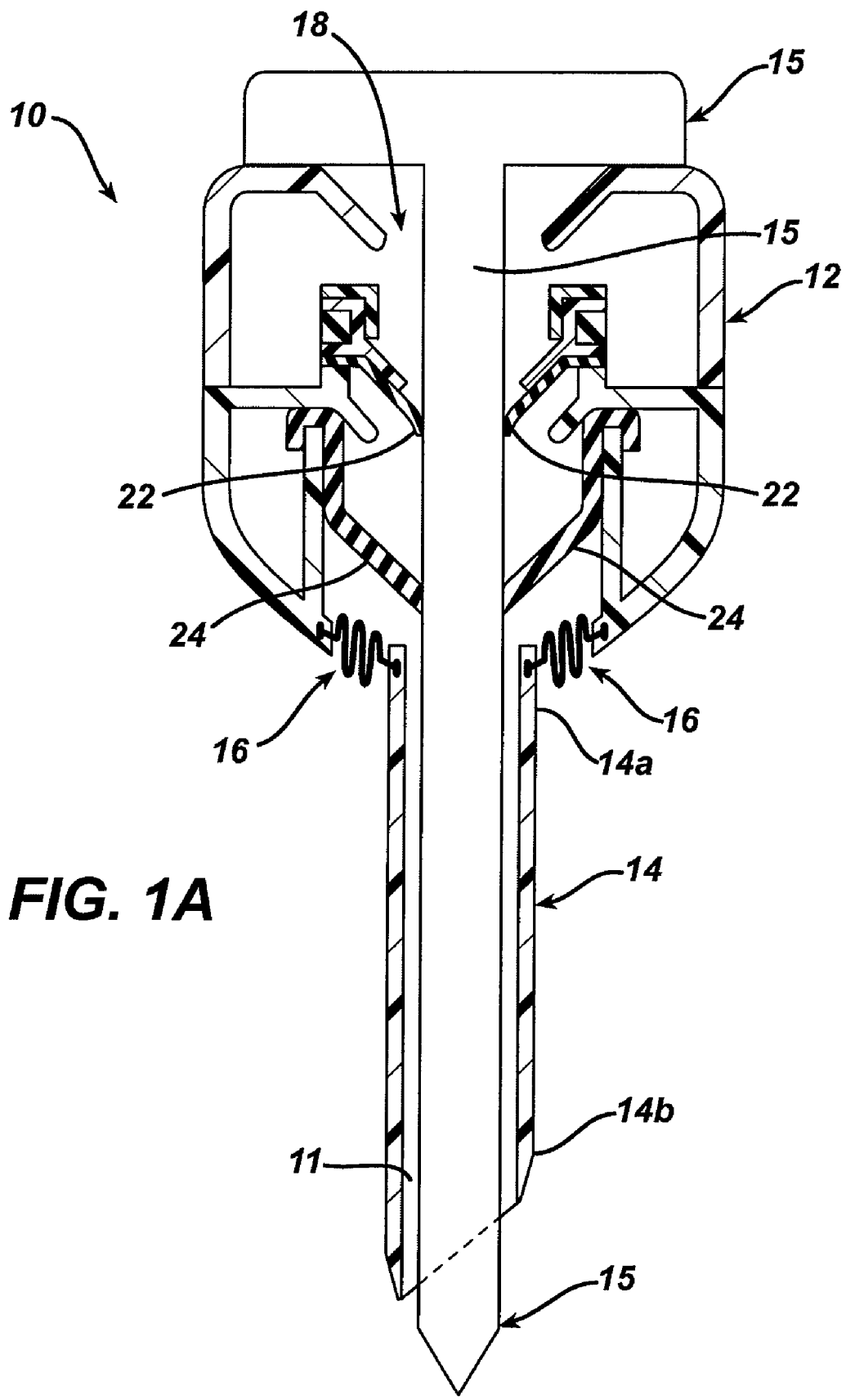
FIG. 1A is a cross-sectional view of one exemplary embodiment of an insertion device.
Figure 1B:
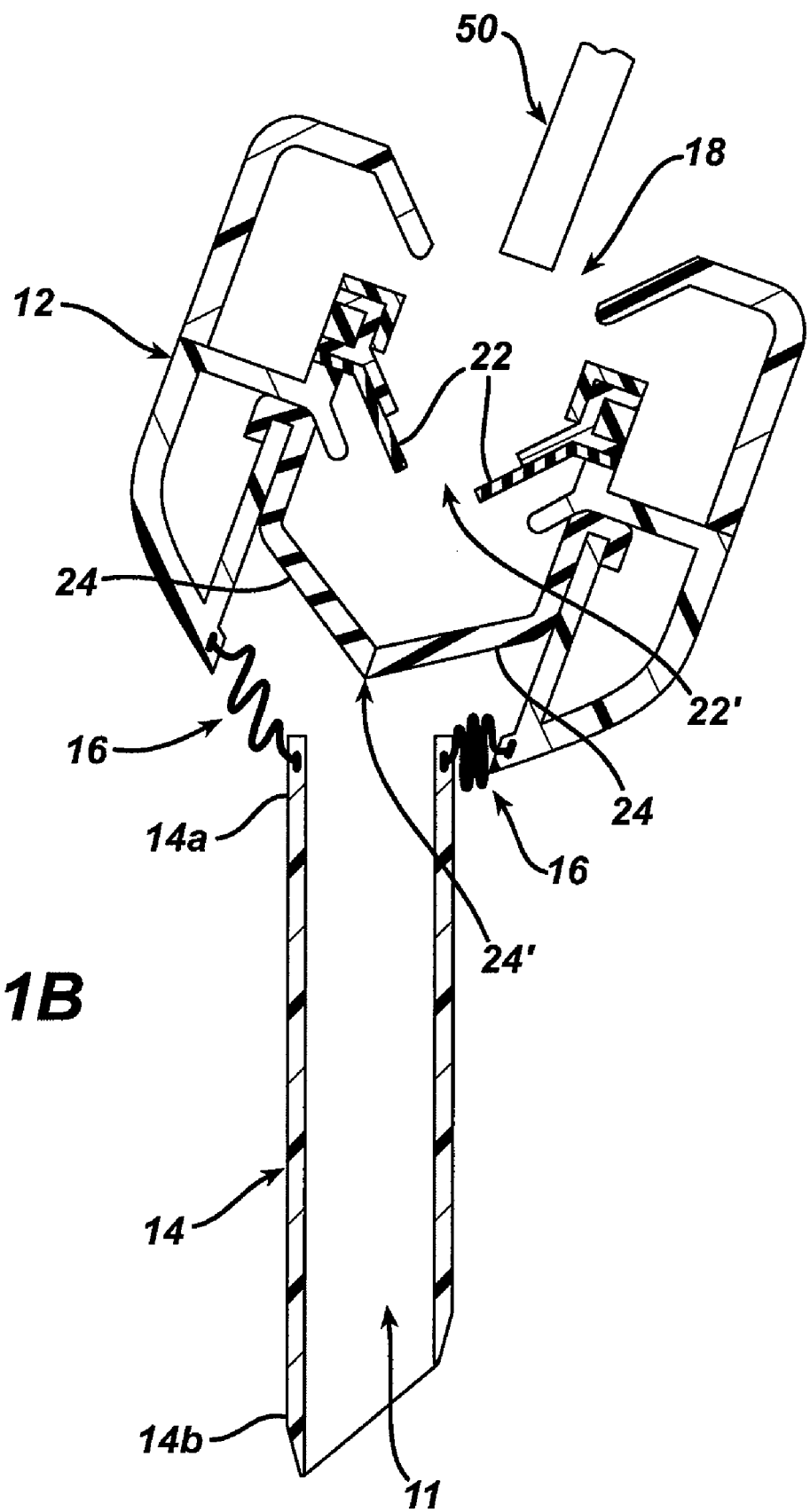
FIG. 1B is a cross-sectional view of the device of FIG. 1A showing the housing angled relative to the cannula.
Figure 1C:
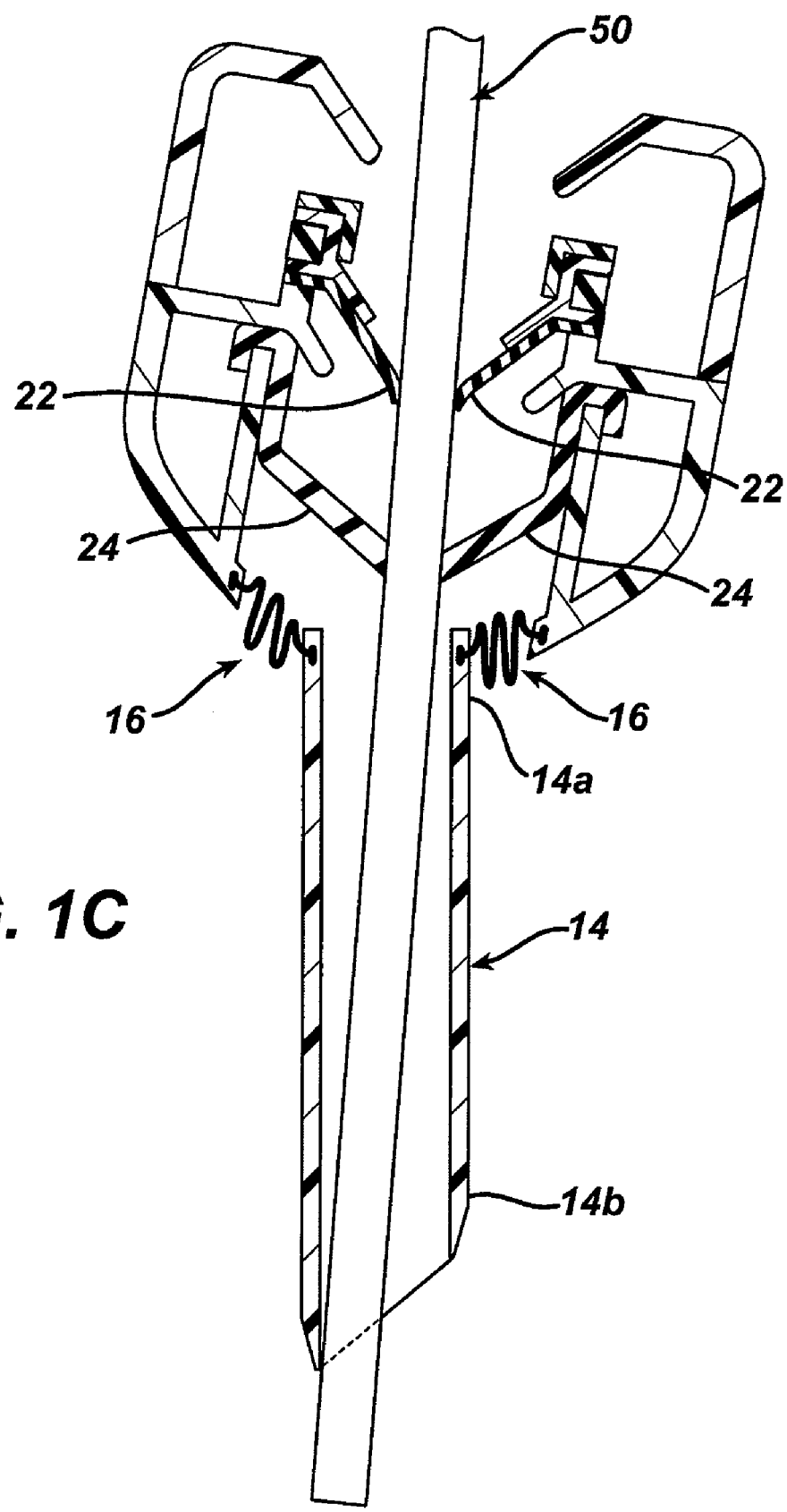
FIG. 1C is another cross-sectional view of the device of FIG. 1A showing the housing angled relative to the cannula.

FIGS. 1A-1C provide one exemplary embodiment of an insertion device having a cannula movably coupled to a housing. In this embodiment, the device is in the form of a trocar, however a person skilled in the art will appreciate that a movable coupling can be used with a variety of other devices. As shown, the device 10 includes an elongate cannula 14 configured for delivery to a body cavity, and further configured to allow for passage of a surgical instrument 50 therethrough. A proximal end of the cannula 14a is movably coupled to a housing 12 thereby allowing the orientation of the housing 12 to move in coordination with a surgical instrument 50 (see FIGS. 1B-1C) passed therethrough. As such, while the housing 12 can be freely manipulated, the cannula 14 can remain stationary thereby eliminating the need to remove and reposition the cannula 14 within the body cavity. The housing 12 can be coupled to the cannula 14 at an intersection point 16 which, as will be discussed in detail below, can be configured in any number of ways to provide such movement. Additionally, any number of seals 22, 24 can be disposed within the housing 12 so as to allow for a closed environment (thereby preventing contamination, escape of insufflation, liquid, etc) during the surgical procedure. In an exemplary embodiment, the seal(s) 22, 24 are fixedly coupled within the housing 12 such that the seal(s) 22, 24 maintain a substantially constant orientation relative to the housing 12 while the housing 12 (and the seal(s) 22, 24) move relative to the cannula 14. In use, the device 10 can be used in various laproscopic and/or endoscopic procedures. For example, the device 10 can be utilized to provide access to an abdominal cavity laprascopically through a peritoneum membrane, or through a natural orifice via natural orifice transluminal endoscopic surgery ("NOTES").

The elongate cannula 14 can have a variety of configurations, but in general it can include a proximal end 14a, a distal end 14b, and an inner lumen 11 extending therebetween and configured to allow for passage of a surgical instrument 50 to a treatment site. The length and/or diameter of the elongate cannula 14 can vary and will typically depend upon the nature of the procedure. Additionally, the material used to form the elongate cannula 14 can vary depending upon the nature of the procedure. For example, some procedures will require a rigid cannula 14 (e.g., laparascopic procedures) and other procedures may require the use of a flexible cannula 14 (e.g., endoscopic procedures). The elongate cannula 14 can be made flexible using various techniques. For example, the cannula 14 can be formed from a flexible material, and/or the cannula 14 can include one or more features formed therein to facilitate such flexibility, such as a plurality of cut-outs or slots. The elongate cannula 14 can also include regions that vary in flexibility. For example, certain portions of the cannula 14, such as the distal portion, can be more rigid than other portions of the cannula 14, such as the proximal portion, to correspond to the shape of a body lumen through which the cannula 14 is being inserted. This can be achieved by forming the cannula 14 from different materials, varying the diameter or thickness of the cannula 14, or using various other techniques know in the art. A person skilled in the art will appreciate that the cannula 14 can have virtually any configuration that allows the cannula to flex as it is inserted through a tortuous body lumen. The cannula 14 can also include other features to facilitate use, such as one or more spiral wires embedded therein and configuration to preventing kinking of the cannula.

As mentioned above, the cannula 14 terminates at a distal end 14b. As will be apparent to those skilled in the art, the distal end 14b can be configured in various manners so as to facilitate passage of the cannula 14 through tissue. For example, as shown, the distal end 14b can be angled. In other embodiments, the distal end 14b can be tapered and/or it can include various protrusions, etc. In other embodiments, the elongate cannula 14 can be used in combination with an obturator 15 (i.e., to form a trocar assembly) wherein the obturator 15 facilitates passage of the elongate cannula 14 through tissue (e.g., the cavity wall). As such, any such insertion device 10 configured to provide passage through a body cavity wall is within the spirit and scope of the present invention.

As mentioned above, the elongate cannula 14 includes a proximal end 14a which is movably coupled to a housing 12. The housing 12 can have a variety of configurations. In the illustrated embodiments, the housing 12 generally includes a proximal opening 18 in communication with the inner lumen 11 of the elongate cannula 14 such that a surgical instrument 50 can be delivered to the inner lumen of the cannula 14 (and ultimately to the treatment site) via the proximal opening 18 of the housing 12. Further, the housing 12 can be configured in various manners so as to allow for a substantially closed environment during passage and/or withdrawal of the surgical instrument thereby preventing liquids and/or insufflation from exiting the elongate cannula 14. For example, in the embodiment of FIG. 1A, the housing 12 includes a first seal 22 (e.g., an outer seal) and a second seal 24 (e.g., an inner seal) disposed within the housing 12. Each seal 22, 24 includes a central aperture 22', 24' configured to allow a surgical device to pass therethrough. The seals 22, 24 can be formed from any of a variety of well known materials (e.g., various polymers or polymer mixtures), and various seal configurations known in the art can be used, including zero closure valves, such as flapper or duck bill valves, and septum valves, etc. Additionally, the seals 22, 24 can be coupled to the housing 12 in any of a variety of well known manners. For example, the seals 22, 24 can be movably coupled relative to the housing 12. In an exemplary embodiment, the seals 22, 24 are fixedly coupled relative to the housing 12. As will be described in detail below, the fixedly coupled seals 22, 24 can move in conjunction with the housing 12 relative to the elongate cannula 14 so as to align the aperture 22', 24' of each seal 22, 24 with a surgical instrument 50 passed therethrough such that the seals 22, 24 can provide an effective sealing thereby maintaining a substantially closed environment.

As indicated above, the housing 12 is movably coupled to the proximal end 14a of the elongate cannula 14. As such, following delivery and positioning of the elongate cannula 14 within the body cavity, the housing 12 can be manipulated relative to the cannula 14 thereby facilitating delivery of a surgical instrument 50 through the housing 12, into and through the inner lumen of the cannula 14, and to the treatment site. As also discussed above, such movement of the housing 12 can optimize the orientation of any seals 22, 24 fixedly disposed therein so as to increase the effectiveness of the seals 22, 24 ability to provide a closed environment. In other words, since the housing, and thus the seals 22, 24, can move with the instrument, deformation of the seals 22, 24 resulting from off-axis delivery of the instrument 50 is eliminated. The coupling between the housing 12 and the cannula 14 can be configured so as to provide the housing 12 with a wide range of motion relative to the cannula 14. For example, the coupling can allow for the housing 12 to be angled, tilted and/or pivoted various amounts relative to the cannula 14. As an example, FIG. 1B shows the housing 12 about to receive a surgical instrument 50, and positioned at an angle relative to the cannula 14 so as to align a proximal opening 18 of the housing (as well as the apertures 22', 24' of the seals 22, 24 disposed therein) with the instrument 50 to be inserted therethrough. FIG. 1C shows the housing 12 with a surgical instrument 50 already positioned through the cannula 14 such that the instrument 50 can be used to position the housing 12. The use of a movable housing 12 facilitates delivery of any type of surgical instrument 50, and also allows for preservation of a closed environment in those procedures where the instrument 50 is being delivered at an angle relative to the elongate cannula 14. The seals 22, 24 can also maintain an effective seal with the surgical instrument 50 even as the instrument is angled to perform the desired procedure.

The housing 12 can be movably coupled to the proximal end 14a of the elongate cannula 14 using a variety of techniques. In general, any coupling and/or mechanism capable of providing a seal between the housing 12 and the proximal end 14a of the cannula 14, and also capable of providing the desired movement of the housing 12 relative to the cannula 14, is within the spirit and scope of the present invention. As shown in FIGS. 1A-1C, the housing 12 can be coupled to or formed on the proximal end 14a of the cannula 14 at an intersection point 16 configured to provide movement of the housing 12 relative to the elongate cannula 14. The intersection point 16 can include a flexible material, such as a bellows as shown, extending between and connecting the cannula 14 and the housing 12. In the illustrated embodiment, the intersection point 16 is located between a proximal most end of the cannula 14 and the distal end of the housing 12, and thus the bellows has a circular shape that connects a circular portion of the housing 12 to a circular portion of the cannula 14. The bellows thus forms a sealed connection between the lumen in the housing 12 and the lumen in the cannula 14. The intersection point 16 can, however, be positioned at various other locations, including along a portion of the cannula 14 and/or a portion of the housing 12. In use, the bellows 16 can flex, expand, contract, or otherwise move so as to provide the desired movement of the housing 12.

Figure 1D:
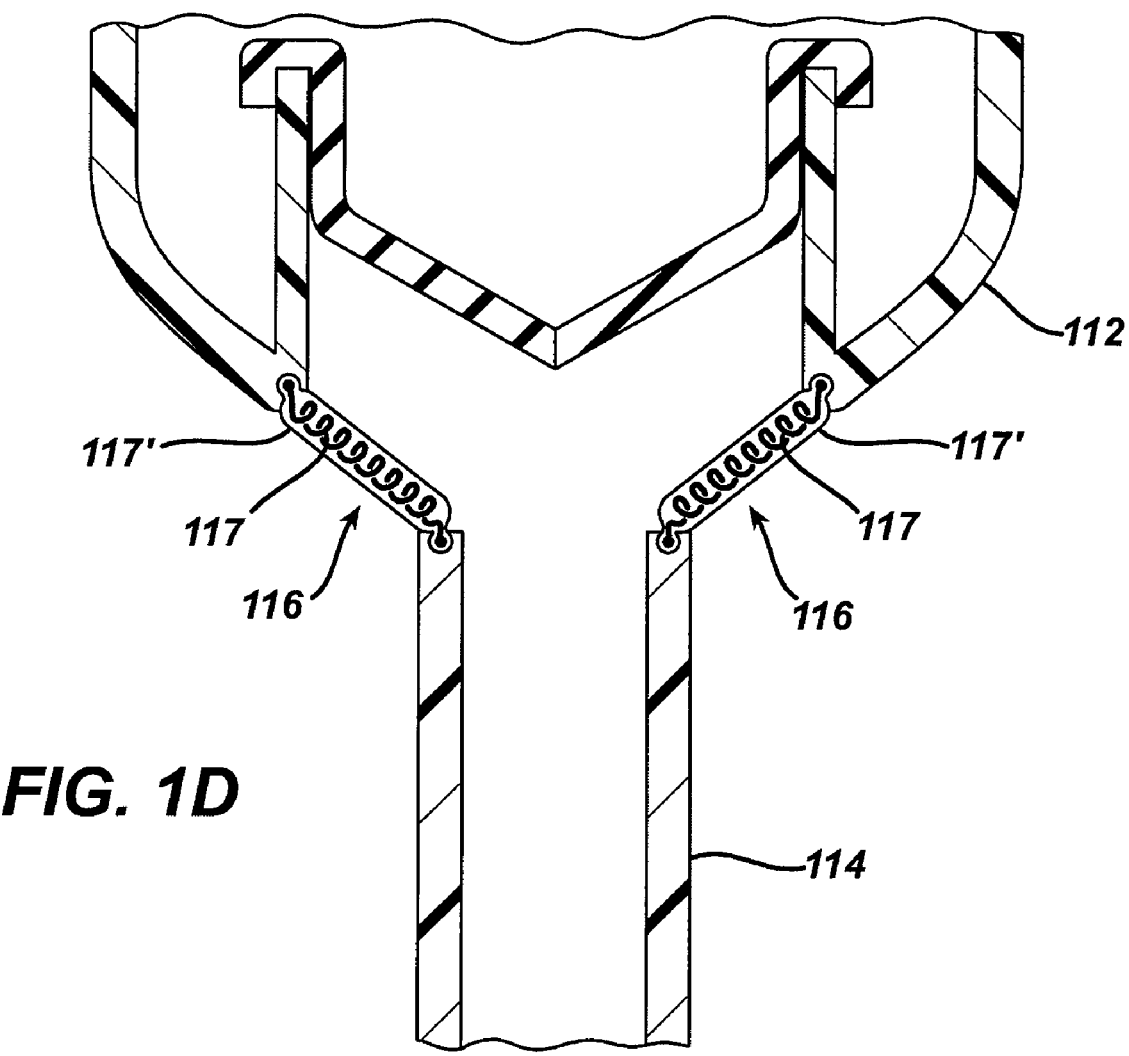
FIG. 1D is a cross-sectional view of an alternative embodiment of an intersection point utilized in the device of FIG. 1A.

A person skilled in the art will appreciate that a variety of flexible or movable materials can be used to allow movement between the housing and the cannula. For example, the intersection point can include a spring or spring-like seal. FIG. 1D shows an intersection point 116 having a spring 117 extending between the housing 112 and cannula 114. In such an embodiment, the spring 117 can be disposed within a covering 117' capable of formed a sealed pathway between the housing 112 and the cannula 114 while also conforming to the movements of the spring 117. As will be apparent to those skilled in the art, the covering 117' can be formed from any of a wide range of materials (e.g., virtually any type of polymer or other biocompatible material).

Figure 2:
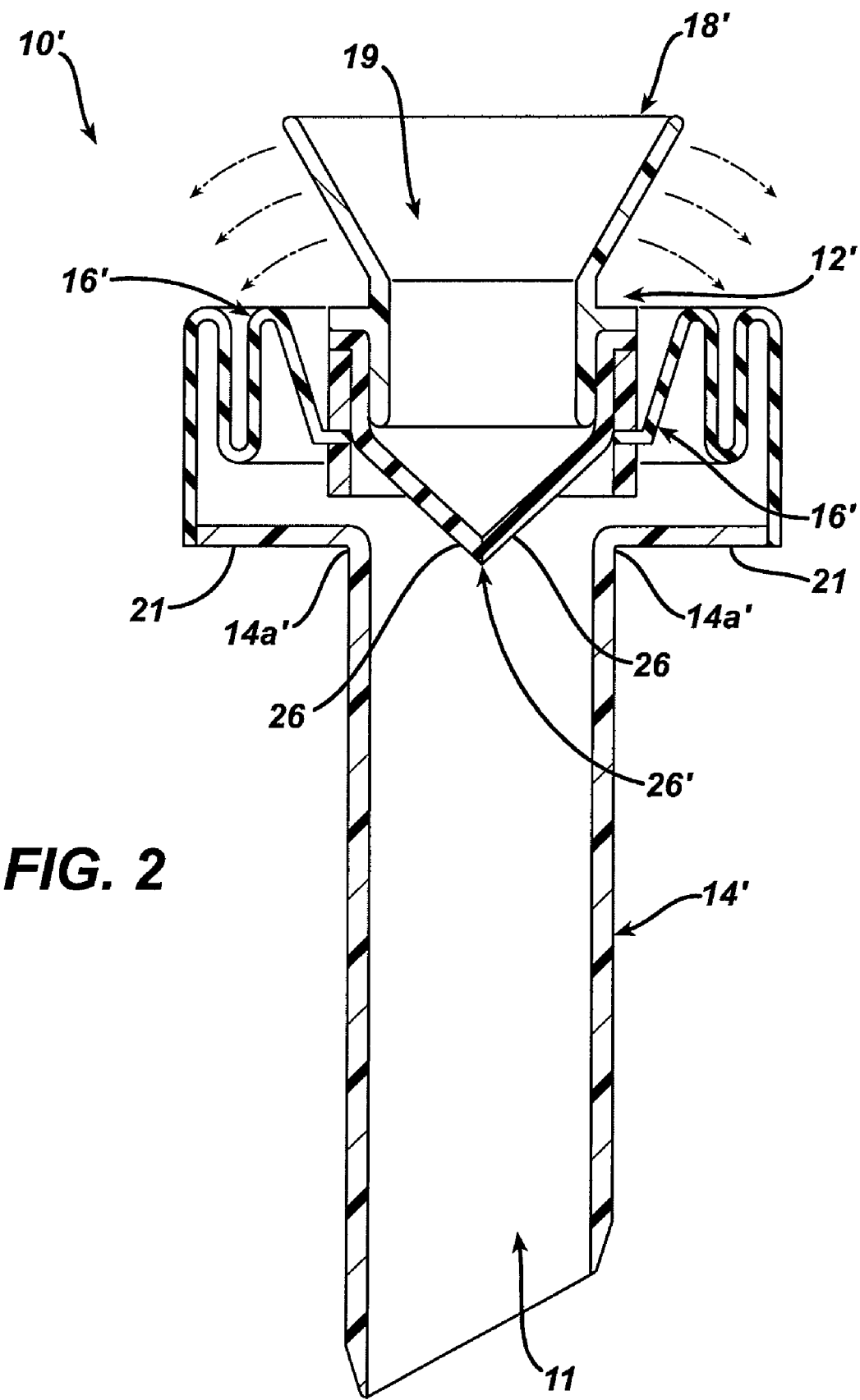
FIG. 2 is a cross-sectional view of another exemplary embodiment of an insertion device.

FIG. 2 provides another exemplary embodiment of an insertion device 10' having a housing 12' movably coupled to an elongate cannula 14'. Similar to the embodiment described above, the insertion device 10' is coupled to the housing 12' at an intersection point 16'. However, in this exemplary embodiment, the housing 12' includes a single seal element 26 fixedly disposed therein. Additionally, a proximal opening 18' of the housing 12' is in communication with a funnel-shaped lumen 19 configured to guide a surgical instrument through a central aperture 26' of the seal 26. Like above, the insertion device 10' is movably coupled to the elongate cannula 14' at an intersection point 16' formed from a flexible and/or deformable material thereby allowing the housing 12' to be moved/angled in a variety of directions (as indicated by arrows) to facilitate positioning of the housing 12' and seal aperture 26' relative to a surgical instrument 50 to be introduced therethrough. While the location of the intersection point can vary, as shown, the proximal end 14a' of the cannula 14' includes a flange or rim 21 formed thereon, and the flexible material extends from an outer edge of the rim 21 and is free to move relative to the cannula 14. The distal end of the housing 12' is not connected to the cannula 14', and thus the entire housing 12' is free to pivot and otherwise move relative to the cannula 14'. A person skilled in the art will appreciate that the particular location of the intersection point 16' can vary, and in other embodiments the intersection point 16' containing the movable connection can be located along a portion of the cannula 14' or along a portion of the housing 12'. The particular location may depend on the type of device and the intended use.

Additionally, various embodiments of a method are provided herein for delivering a surgical instrument to a treatment site. The methods can include any procedure having a surgical instrument delivered to a treatment site via a housing movably coupled to a cannula. For example, the method can include laparascopic and/or endoscopic procedures. Additionally, the method can be configured to allow for access to any number of cavities so as to perform any number of distinct procedures. In general, an exemplary method can include delivering an elongate cannula to a body cavity, and moving a housing coupled to a proximal end of the cannula so as to optimize the orientation of the housing (and seals disposed therein) relative to a surgical instrument passed or to be passed therethrough. As discussed above, moving the housing can substantially eliminate any deformation in the seal resulting from off-axis delivery of a surgical instrument thereby providing a better seal between the housing and the instrument.

In one exemplary embodiment, a cannula is inserted through tissue such that the cannula provides a working channel extending to a treatment site. An instrument can be inserted through the cannula, and positioned offset from an axis of the cannula such that a housing movably coupled to the cannula pivots relative to the cannula so as to move with the instrument. In another exemplary embodiment, a portion of an elongate cannula can be delivered to a body cavity so as to provide surgical access to a treatment site within the cavity. A housing can be moved relative to the cannula so as to align a proximal opening of the housing with a surgical instrument, and the surgical instrument can be delivered to the treatment site via the inner lumen of the cannula.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An insertion device, comprising:
    a cannula having a proximal end, a distal end, and a lumen extending therebetween, the lumen configured to allow for passage of a surgical device to a treatment site; and
    a housing having a proximal end and a distal end located proximal to the proximal end of the cannula, wherein the distal end of the housing is movably coupled to the proximal end of the cannula by a flexible member, the housing having a lumen therethrough in alignment with the lumen in the cannula.

2. The insertion device of claim 1, further comprising at least one seal disposed in the housing and extending across the lumen in the housing.

3. The insertion device of claim 2, wherein the seal is fixedly disposed within the housing.

4. The insertion device of claim 2, wherein the at least one seal comprises a first seal and a second seal.

5. The insertion device of claim 1, wherein the flexible member comprises a bellows.

6. The insertion device of claim 1, wherein the flexible member comprises a spring.

7. A trocar assembly, comprising:
    an obturator; and
    a trocar cannula having
        a housing with proximal and distal ends,
        a hollow shaft having a proximal end located distal to the distal end of the housing and movably coupled to the distal end of the housing by a flexible member, and
        a lumen extending through the housing and the hollow shaft for receiving and guiding the obturator through the trocar cannula.

8. The assembly of claim 7, wherein the flexible member extends between the proximal end of the hollow shaft and an opening formed in the distal end of the housing.

9. The assembly of claim 8, wherein the flexible member comprises a bellows.

10. The assembly of claim 8, wherein the flexible member comprises a spring.

11. The assembly of claim 7, further comprising at least one seal disposed in the housing and extending across the lumen in the housing.

12. The assembly of claim 11, wherein the seal is fixedly disposed within the housing.

13. The assembly of claim 11, wherein the at least one seal comprises a first seal and a second seal.

14. A method for processing the assembly of claim 7 for surgery, comprising:
    a) obtaining the assembly of claim 7;
    b) sterilizing the assembly; and
    c) storing the assembly in a sterile container.

15. A method for delivering a surgical instrument to a treatment site, comprising:
    inserting a cannula through tissue such that the cannula provides a working channel extending to a treatment site;
    inserting an instrument through the cannula;
    positioning the instrument offset from an axis of the cannula such that a housing having a distal end located proximal to the proximal end of the cannula and movably coupled to the proximal end of the cannula pivots relative to the cannula so as to move with the instrument.

16. The method of claim 15, wherein the cannula includes an obturator disposed therein, and inserting the cannula comprises penetrating obturator with cannula disposed therearound through tissue.

17. The method of claim 15, wherein the housing includes a seal, and the seal maintains a sealed relationship with the instrument as the housing pivots relative to the cannula.

18. The method of claim 15, further including sterilizing the insertion device after at least one use.

* * * * *